United States Patent [19]
Agathos

[11] Patent Number: 6,165,216
[45] Date of Patent: *Dec. 26, 2000

[54] HUMAN CARDIAC VALVE PLACEMENT WITH MARINE MAMMAL VENTRICULAR OUTFLOW (AORTIC OR PULMONARY) VALVE

[75] Inventor: Efstathios Andreas Agathos, 993 Memorial Dr., Cambridge, Mass. 02138

[73] Assignee: Efstathios Andreas Agathos, Cambridge, Mass.

[*] Notice: Under 35 U.S.C. 154(b), the term of this patent shall be extended for 215 days.

[21] Appl. No.: 08/678,196

[22] Filed: Jul. 12, 1996

Related U.S. Application Data

[63] Continuation of application No. 08/492,896, Jun. 20, 1995, abandoned.

[51] Int. Cl.[7] .................................................. A61F 2/24

[52] U.S. Cl. ...................................... 623/2.13; 623/2.42

[58] Field of Search .............................. 623/2, 900, 66, 623/2.13, 2.42

[56] References Cited

U.S. PATENT DOCUMENTS

| | | | |
|---|---|---|---|
| 4,079,468 | 3/1978 | Liotta et al. | 3/1.5 |
| 4,451,936 | 6/1984 | Carpentier et al. | 623/2 |
| 4,793,344 | 12/1988 | Cumming et al. | 128/305 |
| 5,080,670 | 1/1992 | Imamura et al. | 623/2 |
| 5,156,621 | 10/1992 | Navia et al. | 623/2 |
| 5,215,541 | 6/1993 | Nashef et al. | 8/94.11 |
| 5,352,240 | 10/1994 | Ross | 673/2 |
| 5,370,685 | 12/1994 | Stevens et al. | 623/2 |
| 5,439,667 | 8/1995 | Camiener | 435/40.5 |

FOREIGN PATENT DOCUMENTS 21 36 533   9/1984   United Kingdom .

OTHER PUBLICATIONS

Buffalow News, Jan. 14, 1994, VB Research Center Seeks Bio–Tech Firms.

M.I. Ionescu (ed.), *Tissue Heart Valves*, Butterworths, Boston, pp. 32–34, 107–109, 122, 137–150, 146–172, 177 (1979).

W.R.E. Jamieson, "Modern Cardiac Valve Devices—Bioprostheses and Mechanical Prostheses: State of the Art," J. Card. Surg., 8:89–98 (1993).

C.G. Duran, "The Pericardial Heart Valve: An Open Question" in *Replacement Cardiac Valves*, (E. Bodnar and R. Frater eds.), Pergamon Press, New York, pp. 277–285 (1991).

(List continued on next page.)

*Primary Examiner*—Bruce Snow
*Attorney, Agent, or Firm*—Medlen & Carroll, LLP

[57] ABSTRACT

The present invention provides a method of treating human cardiac valve dysfunction, by replacing the existing valve with a novel bioprosthesis of the present invention which comprises a marine mammal ventricular outflow (aortic or pulmonary) valve. The marine mammal ventricular outflow valve is treated by a fixative agent to sterilize, fix, increase the strength of the leaflets and lessen the antigenicity of the tissue valve. Following this step, the marine mammal ventricular outflow valve can either be stent-mounted or can be unstented. The stent-mounted marine mammal ventricular outflow valve can be used to replace a human aortic, mitral, or tricuspid valve, while the unstented marine mammal ventricular outflow valve can be used to replace a human aortic or pulmonary valve. Being a natural trileaflet valve, with symmetrical cusps and no muscle shelf within the leaflet, the marine mammal ventricular outflow valve presents superior hemodynamic advantages over the existing aortic porcine and bovine pericardial valves. The increase thickness of the leaflets result in a long-term durability, without the attendant disadvantages of re-replacing a bioprosthesis. Alternatively, a marine mammal trileaflet valve can be contructed from tissues such as pericardium and fascia lata.

23 Claims, 4 Drawing Sheets-

OTHER PUBLICATIONS

G.I. Grunkemeier et al., "Prosthetic Heart Valve Performance: Long–term Follow–up," Curr. Probl. in Cardiol., 17:362–368 (1992).

C. Weinhold et al., "Kangaroo xenobioprostheses—an advantage in heart valve replacement," Z. Kardiol. 75, Suppl. 2, pp. 251–253 (1986).

Emory and Arom (eds.), *The Aortic Valve,* Hanley & Belfus, Philadelphia, pp. 219–225 (1991).

John W. Kirklin and Brain G. Barratt–Boyes (eds.), *Cardiac Surgery* 2nd edition, Churchill Livingstone, New York, p. 511 (1993).

D.L. Sewell et al., "Prosthetic Valve Endocarditis Caused by *Corynebacterium afermantans* subsp. *lipophilum* (CDC Coryneform Group ANF–1)," J. Clin. Microb., 33:759–761 (1995).

D.J. Lentz et al., "Prevention of Intrinsic Calcification in Porcine and Bovine Xenograft Materials," Trans. Am. Soc. Artif. Intern. Organs, 28:494–497 (1982).

Ishihara et al., "Structure of bovine parietal pericardium and of unimplanted Ionescu–Shiley pericardial valvular bioprostheses," J. Thorac. Cardiovasc. Surg., 81:747–757 (1981).

Hammond et al., "Biological versus mechanical valve," J. Thorac. Cardiovasc. Surg., 93:182–98 (1987).

Jamieson et al., "Carpetier–Edwards supra–annular porcine bioprosthesis—new generation biological valve," Z. Kardiol.,75:245–50, Supp. 2 (1986).

Konstantinov et al., "New Cardiac Bioprosthesis: Theory, Experiments, and 10 Years of Clinical Use," Ann. Thorac. Surg., 48:S79–80 (1980).

Konstantinov et al., "Plastic Surgery for Cardiac Valves: 15 Years' Experience," Ann. Thorac. Surg., 48:S77–8 (1989).

Saggau et al., "Tissue Glue For Sealing Plastic Valves And Bioprothesis In The Canine Aorta," Scand. J. Thor. Cardiovasc. Surg., 16:129–135 (1982).

Rhode et al., "Pressure–volume characteristics of aortas or harbor and Weddel seals," Am. J. Physiol. ,251:R174–R180 (1986).-

HUMAN CARDIAC VALVE PLACEMENT WITH MARINE MAMMAL VENTRICULAR OUTFLOW (AORTIC OR PULMONARY) VALVE

This is a continuation of application Ser. No. 08/492,896 filed on Jun. 20, 1995 now abandoned.

FIELD OF INVENTION

This invention relates to the field of surgical implants, and in particular to a method of treating cardiac valve dysfunction in a human patient by replacing the existing valve with a marine mammal ventricular outflow (aortic or pulmonary) valve.

BACKGROUND

The normal human heart is a four chamber muscular organ which serves as the main pump of blood of the circulatory system. Systemic venous blood enters the right atrium through the superior and inferior vena cavae; then through the tricuspid valve enters the right ventricle where it is pumped to the pulmonic artery and the lungs through the pulmonary valve. Blood from the lungs enters the left atrium through the four pulmonary veins; then through the mitral valve enters the left ventricle where it is pumped to the aorta and the rest of the body through the aortic valve. The function of these valves is to allow blood flow easily through them in one direction by opening the leaflets and preventing blood from regurgitating back by closing the leaflets. In some individuals one or more valves may not function normally, usually as a result of disease-induced valve damage, degeneration or a congenital defect. Some valves may become stenotic, thus impeding forward blood flow, and some valves may become incompetent, thus allowing blood to backflow through them. Both conditions can lead to life threatening conditions. For the last 35 years, severe valve dysfunction has been treated by replacing the valve with a mechanical prosthesis, or alternatively, with a tissue valve (i.e., a valve of human or animal tissue). Tissue valves have the advantage of low thrombogenicity, therefore they do not need long term anticoagulation, as this is the case for mechanical valves, thus eliminating the potential clinical complications, expense and patient inconvenience. Tissue valves can be categorized as allografts (usually aortic valves from cadavers, also referred as homografts) or xenografts (animal heart valves). In addition some aortic valves have been replaced by autografts (Ross procedure), which is a pulmonary valve from the same patient which in turn is replaced with an allograft (homograft) or a xenograft ("Tissue Heart Valves", ed. by M. I. Ionescu, publisher Butterworth Inc., Boston Mass., U.S.A., 1979, particularly at pp. 146–172). Due to difficulties in sterilization, storage, and availability of multiple valve sizes, allografts (homografts) are not widely used by cardiac surgeons. Ross procedure is a lengthy and technically very demanding operation not widely used either. Xenografts from the other hand are quite commonly used for human cardiac valve replacement. These are either porcine aortic valves or valves constructed from bovine pericardium (W. R. E. Jamieson; J. Card. Surg., 1993;8;89–98). A variety of sizes are readily available. Both types of xenografts have to be first treated with an agent, typically glutaraldehyde, to fix the valve tissue, sterilize it, and decrease its antigenicity. In particular the porcine aortic xenograft has been used for cardiac valve replacement, both as stented (mounted in a frame) or unstented ("Tissue Heart Valves", supra, particularly at pp. 32–34, 107–109, and 177). Because unstented valves minimize turbulence they should reduce thrombosis and embolism. However, they require a more difficult operative procedure for insertion than the stented valves and can only be used in the aortic portion. The porcine aortic valve is a trileaflet valve, but not identical to the human aortic valve. An important distinction is that the porcine aortic valve has a muscle shelf which extends into one of the valve cusps (the right-coronary cusp). This muscle shelf prevents the right coronary cusp from completely opening, thereby partially obstructing the flow. This obstruction is accentuated in small diameter valves as for example in those of children. Attempts have been made to compensate this problem by either trying to enlarge a patients aortic annulus (the portion of the heart in which the valve is seated) so that a porcine aortic valve having a diameter greater than that of the patient's aortic valve could be used, or by developing a technique in which the right coronary cusp of the porcine aortic valve has been replaced with a non-coronary cusp from another porcine aortic valve. However, such techniques require additional manipulations of the patient's aortic annulus or the porcine aortic valve, with their attendant difficulties and expense. Bovine pericardial valves cannot be used in the mitral position due to their high thrombogenicity and structural failure (C. G. Duran, in "Replacement Cardiac Valves" edited by E. Bodnar & R. Frater, publisher Pergamon Press, Inc. New York 10523 USA, 1991, pp. 277–285) and their manufacture requires a lot of technical manipulations that increase their market cost. Both porcine aortic and bovine pericardial valves start to fail within five years from their implantation and eventually all require replacement in approximately ten years (G. I. Grunkemeier et al., Curr. Probl. Cardiol. 1992; 17;362–368). The use of porcine pulmonary valve as was suggested by Ross (U.S. Pat. No. 5,352,240, issued in 1994) has not been widely accepted by cardiac surgeons, as the pulmonary leaflets are very thin and friable and soon fail after the initial implantation. The Wain bioprosthetic cardiac valve (United Kingdom Patent Application No. 8303479, Publication No. 2 136533A, filed by Wain in 1983) represents a valve too cumbersome to manufacture, without any obvious advantage over the existing bioprosthetic valves and without durability. New animals have been tested such as Kangaroo (C. Weinhold et al., Z. Kardiol. 75, Suppl. 2, pp.251–253, 1986), and although promising the limited animal stock will fail to provide enough valves to cover the international market. In addition to the aforementioned limitations, porcine aortic or pulmonary valves are not favored by Muslim patients while bovine pericardial valves are not favored from Buddhists patients and other similar religious groups, thereby excluding a large portion of the world market.

SUMMARY OF THE INVENTION

The present invention provides a method of treating human cardiac valve dysfunction, by surgically replacing the existing valve with a novel bioprosthesis of the present invention which comprises a marine mammal ventricular outflow (aortic or pulmonary) valve. Preferably, the marine mammal ventricular outflow valve is treated with a fixative, such as glutaraldehyde, polyepoxy compound or any other proper agent to fix, sterilize, increase the strength of the leaflets and reduce the antigenicity of the valve tissue. Following this step the marine mammal ventricular outflow valve can either be stent-mounted or can be unstented. The marine mammal ventricular outflow valve has superior hemodynamic performance than the existing porcine aortic or bovine pericardial valve and in addition better durability due to the increase thickness of the leaflets.

Accordingly, several objects and advantages of my invention are to provide a method of treating valve dysfunction in a human patient, by replacing the existing valve with a novel bioprosthesis of the present invention which comprises a marine mammal ventricular outflow (aortic or pulmonary) valve. The marine mammal aortic and pulmonary valves are trileaflet valves which as in humans have no muscle shelf attached on the coronary cusps or any other cusps make them performing with obvious advantages. As a result of this fact there is no need for further technical modification and complex operations as is the case of using porcine aortic or bovine pericardial valves. The marine mammal ventricular outflow bioprosthesis can be easily produced and used either as an unstented valve or as a stented one after having been mounted on a frame. Due to the consistency of the leaflets, which have higher content of collagen and elastic fibers, the marine mammal ventricular outflow valves are more durable than any other existing bioprosthetic valves, thereby reducing the likelihood of reoperation (which carries a high morbidity and mortality rate), offering tremendous financial benefits and convenience to patients, health insurance companies and organizations.

Additional objects and advantages of this novel bioprosthesis is the acceptance from Muslim countries and Buddhists (i.e., India) which represent a very large part of the world market, otherwise difficult to penetrate. As the marine mammals ventricular outflow valves can be harvested from cadaveric animals (i.e., those accidentally caught during commercial fishing activities, or during population control programs in Canada), the source of these bioprosthetic valves become inexpensive, maintaining an ample supply (an estimated 300,000 valves per year, large enough to supply the international market), and at the same time sensitizing people and Foreign Governments to even better protecting these endangered animals. Still further objects and advantages will become apparent from a consideration of the ensuing description and accompanying drawings.

In one embodiment, the present invention contemplates a method of treating a human patient, comprising surgically implanting a marine mammal ventricular outflow valve in said patient. It is not intended that the present invention be limited by the nature of the human patient, the particular dysfunction, or the specific valve that is replaced. In one embodiment, the present invention contemplates a method of treating aortic, mitral or tricuspid valve dysfunction in a human patient, comprising replacing the existing dysfunctional valve with a marine mammal ventricular outflow valve. In another embodiment, the patient's existing pulmonary valve is replaced with said marine mammal valve.

In a further embodiment, the marine mammal valve is a fixed (i.e. treated with a fixative) and sterilized stent-mounted valve. In still another embodiment, the marine mammal valve is a fixed and sterilized whole excised unstented valve. The marine mammal valve may be an aortic or pulmonary valve; on the other hand the marine mammal valve can be a trileaflet bioprothesis constructed from marine mammal tissues selected from the group consisting of pericardium or fascia lata.

It is contemplated in one embodiment that the marine mammal valve comprises a section of ascending aorta. In another embodiment, the marine mammal valve comprises a section of pulmonary artery.

In a preferred embodiment, the marine mammal valve has an inlet side and further comprises a flexible sewing skirt extending from said inlet side to facilitate suturing of the valve in said patient.

As noted above, the present invention contemplates a fixed, marine mammal ventricular outflow valve. It is not intended that the present invention be limited by the particular marine mammal. In one embodiment, the marine mammal is selected from the group consisting of seals, sea lions, dolphins, porpoises, and whales.

REFERENCE NUMERALS 6 marine mammal aortic valve
8 aortic annulus
10 cusps or leaflets
12 segment of the marine mammal ascending aorta
14 orifice of the right coronary artery
16 orifice of the left coronary artery
18 flexible sewing ring
20 marine mammal pulmonary valve
22 pulmonary annulus
24 segment of pulmonary artery
26 conventional stent
28 flexible legs
30 sewing ring

DESCRIPTION OF THE INVENTION AND EMBODIMENTS

Figure 1:
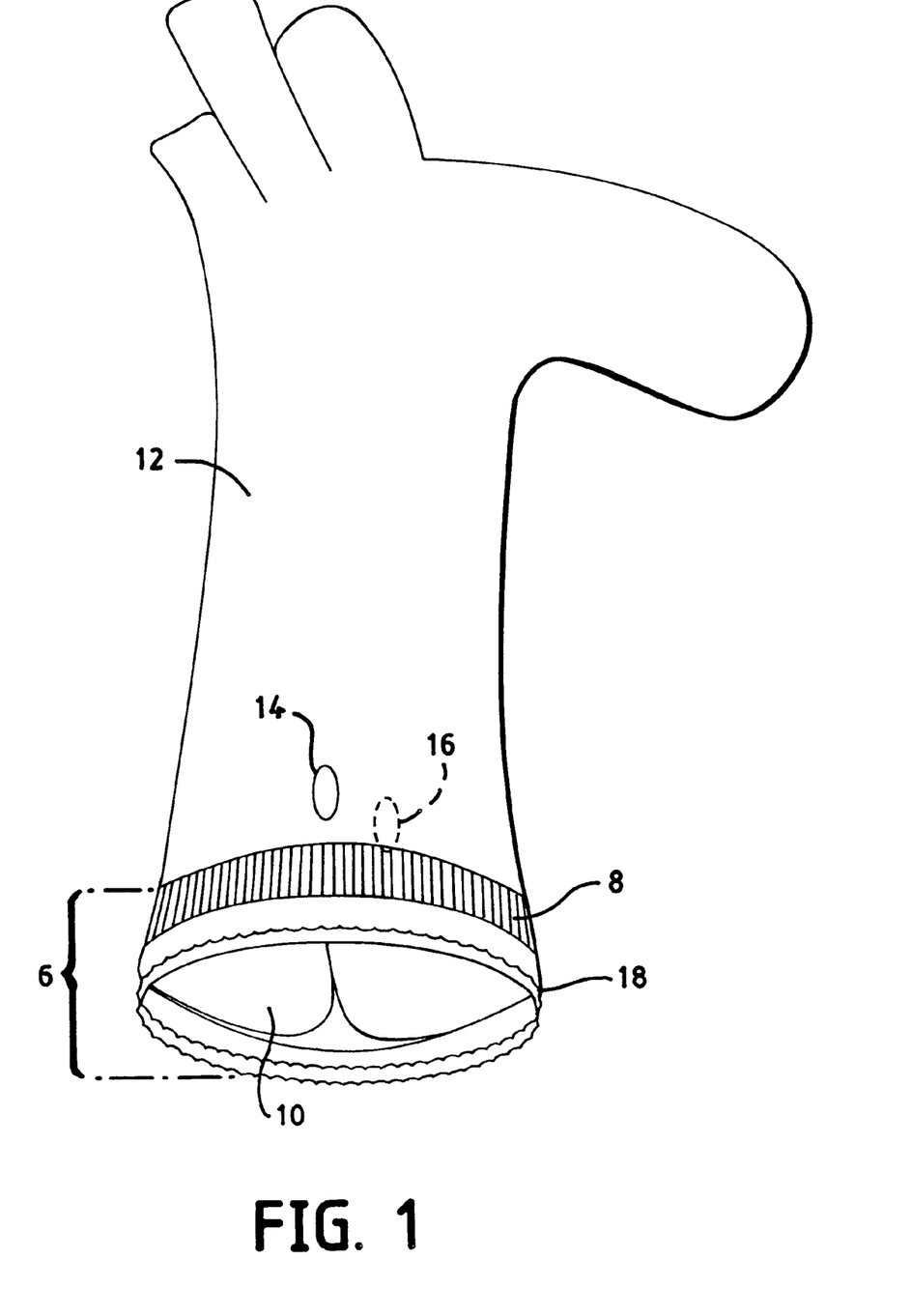
FIG. 1 is a perspective view of an unstented marine mammal aortic valve with an attached segment of ascending aorta, showing the presence of a sewing skirt which has been sutured adjacent the inflow side of the valve.

FIG. 1 shows an unstented marine mammal aortic bioprosthesis. An excised marine mammal aortic valve 6, is shown, which actually consists of an aortic annulus 8 and three cusps or leaflets 10 attached to the annulus 8. A segment of the marine mammal ascending aorta 12 has been excised along with the aortic valve 6. The two coronaries arteries have been excised and the orifice of the right coronary artery 14 and the orifice of the left coronary artery 16 have been slightly enlarged. At this point the unitary combination of the valve 6 along with the segment 12 would be treated with a fixative such as glutaraldehyde, a polyepoxy compound, or any other suitable agent, to fix and decrease the antigenicity of the tissue. An unstented bioprosthesis for human cardiac valve replacement can then be prepared by suturing a flexible sewing ring 18, made of synthetic polymer, such as those sold under the trademarks DACRON or TEFLON, to the aortic annulus 6. This unstented marine mammal aortic bioprosthesis can then be sterilized and stored in the same manner as known for unstented porcine aortic valves.

Figure 2:
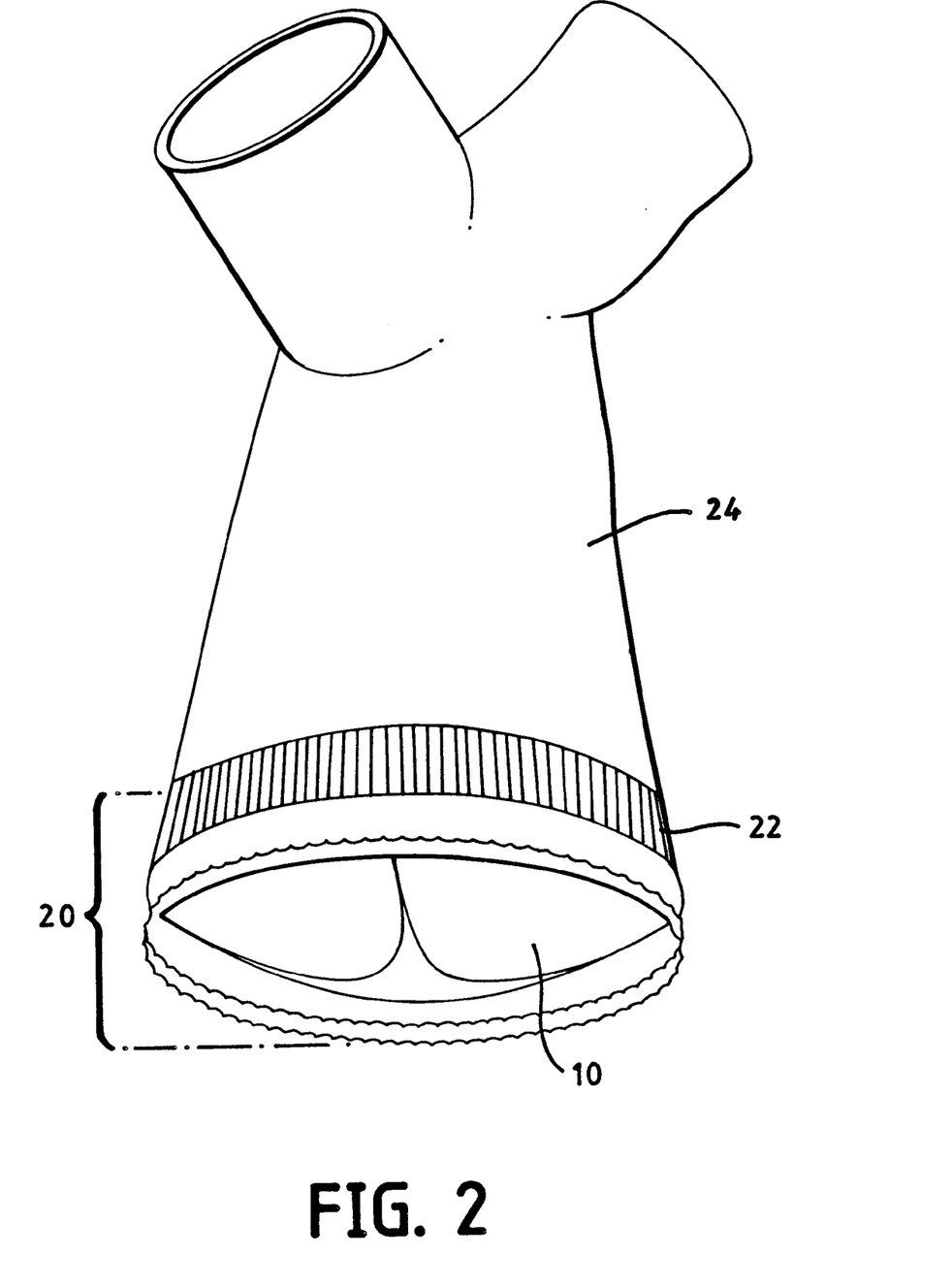
FIG. 2 is a perspective view of an unstented marine mammal pulmonary valve with an attached segment of pulmonary artery, showing the presence of a sewing skirt which has been sutured adjacent the inflow side of the valve.

FIG. 2 shows an unstented marine mammal pulmonary bioprosthesis. An excised marine mammal pulmonary valve 20, is shown, which actually consists of a pulmonary annulus 22 with three cusps or leaflets 10 attached to it. A segment of pulmonary artery 24 has been excised along with the pulmonary valve 20. At this point the unitary combination of the valve 20 along with segment 22 can be treated in exact the same way as was described in the previous paragraph for the unstented marine mammal aortic bioprosthesis. This unstented marine mammal pulmonary bioprosthesis can then be sterilized and stored in the same manner as known for unstented porcine aortic valves.

Figure 3:
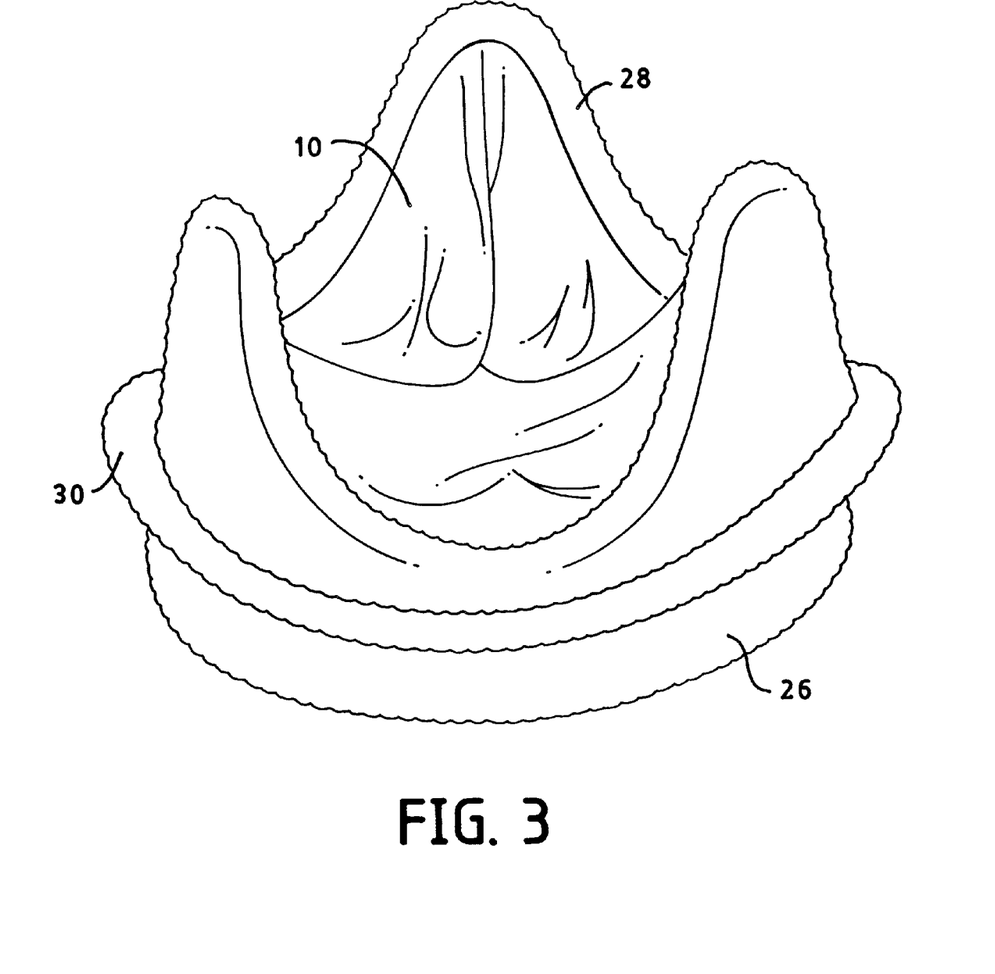
FIG. 3 is a perspective view of a stent-mounted marine mammal ventricular outflow (aortic and pulmonary) valve.
Figure 4:
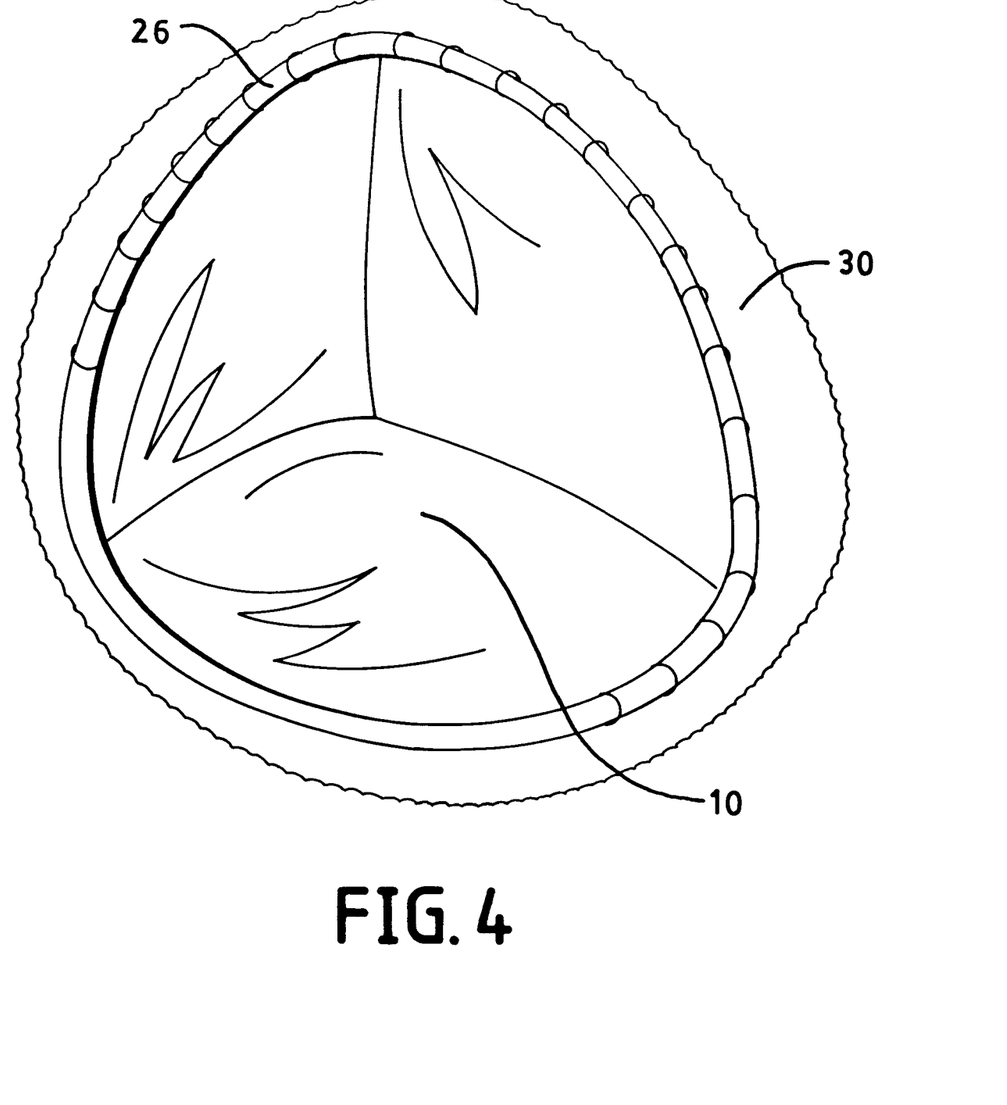
FIG. 4 is a perspective view of a stent-mounted marine mammal ventricular outflow (aortic or pulmonary) valve from the inflow side.

A stented marine mammal ventricular outflow bioprosthesis (essentially same design characteristics for both the aortic and the pulmonary valve) is shown in FIG. 3 and FIG. 4 (inflow view). After having fixed the tissues, as has been described above, the segment of the ascending aorta 12, or the segment of the pulmonary artery 24 is removed, and the remaining valve structure 6 or 20 is sutured to a conventional stent 26, which is made of metal or any other suitable material. This stent 26 has three upstanding, symmetrical and inwardly flexible legs 28 and a conventional sewing ring 30 to facilitate implantation. Both the structure of stent 25 and the manner of suturing the marine mammal ventricular outflow valve (aortic 6 or pulmonary 20) thereto, are analogous to the well known stents and suturing techniques used to prepare a stented porcine aortic valve. For example, see "Tissue Heart Valves", supra., particularly at pp. 32–34, 107–109 and 177. The resulting stented marine mammal ventricular outflow valve can then be sterilized and stored in the same manner, and under the same conditions, as the unstented valves of FIG. 1 and FIG. 2.

The resulting fixed and sterile marine mammal ventricular outflow valves, both stented (FIG. 3 and FIG. 4), and unstented with a sewing skirt (FIG. 1 and FIG. 2), can then be used to replace human cardiac valves with well known and established surgical techniques. For example, the unstented marine mammal ventricular outflow valve with sewing skirt (FIG. 1 and FIG. 2) can replace a human aortic valve using essentially the same techniques as for replacement of a human aortic valve with an allograft or homograft. For example see "Tissue Heart Valves," supra., particularly pp. 137–150, and "The Aortic Valve", ed. Emery and Arom, publisher Hanley & Belfus Inc., Philadelphia, Pa., U.S.A. (1991), in particular pp. 219–225. In the same manner, the stented marine mammal ventricular outflow valve (FIG. 3 and FIG. 4) can be used to replace a human aortic valve using essentially the same surgical technique as used to replace a human aortic valve with a stented porcine aortic bioprosthesis, See, for example, "Tissue Heart Valves", supra., particularly at p. 122, and "Cardiac Surgery", eds. John W. Kirklin & Brian G. Barratt-Boyes, published by Churchill Livingstone Inc., New York, N.Y., U.S.A., second edition (1993), and particularly at p. 511. The stented marine mammal ventricular outflow valve (aortic or pulmonary) is mainly recommended for replacement of human aortic, mitral and tricuspid valves. The unstented marine mammal ventricular outflow valve (aortic or pulmonary) is mainly recommended for replacement of human aortic or pulmonary valves.

PREFERRED EMBODIMENT—OPERATION

The marine mammal ventricular outflow valves (aortic and pulmonary) are naturally trileaflet valves. The leaflets have a thick layer of collagen and elastic fibers, they lack of muscle shelf (i.e., as is the case in the porcine aortic valves) thus presenting no obstruction to bloodflow, opening in full extent with the minimum of work required, and having an excellent coaptation in the close position, preventing therefore any backflow (leakage). For example the aortic valve of an adult harbor seal (Phoca Vitulina) was tested for hemodynamic performance in the laboratory. This heart was donated to me by the Northeast Fisheries Science Center, in Woods Hole, Mass., U.S.A. under the Marine Mammal Protection Act Permit #979. This animal was an incidental catch during commercial fishing operations in the Gulf of Maine, U.S.A. having been maintained in the frozen state at a temperature of −20 degrees of Celsius. The aortic valve was harvested as a fresh xenograft and mounted to a silicone rubber tube. The unitary combination of the aortic valve and silicone tube was then placed in a "pulse duplicator" which is a standard valve tester complying to the requirements of the International Standards Organization (ISO); ISO 5840, Cardiovascular Implants-Cardiac Valve Prosthesis. The test followed the Federal Drug Administration (FDA) guidelines for new valve tests, which is to simulate hemodynamic conditions similar to that of an adult human normal functioning heart under different level of activity. Therefore the simulation is that of a beating heart at 70 beats a minute, with an aortic pressure of 100 mmHg, a ventricular pressure of 50 mmHg and a cardiac output (volume of blood pumped by the ventricle per minute) of 3, 4 and 5 liters per minute. For each cardiac output there were 10 different measurements and the computerized results were as shown below:

| Cardiac Output (L/min) | 3 | 4 | 5 |
| --- | --- | --- | --- |
| Transaortic Pressure Gradient (mmHG) | 0.93 | .24 | 1.93 |
| Leakage Backflow (%) | 3.42 | 2.93 | 2.60 |
| Leakage Volume (ml) | 1.81 | 2.02 | 2.17 |
| Closing Energy (Joulesx1E-3) | 52.7 | 65.3 | 71.9 |
| Effective Aortic Orifice (cm$^2$) | 3.46 | 3.76 | 3.76 |

These results show the excellent hemodynamic performance of the marine mammal ventricular outflow valve (i.e., the harbor seal aortic valve), which is superior to any other bioprosthetic valve tested before. An other obvious advantage of the present invention is the thicker consistency of the leaflets (due to higher level of collagen and elastic fibers) making them more durable than the existing bioprosthetic valves. It is of importance to stress that the cadaveric marine mammal ventricular outflow valves (if harvested within 20 hours of the animal death), retain all of the superb functions and characteristics and as so there is no need for sacrificing live animals for this purpose. Furthermore the use of marine mammal valves as a natural byproduct, will eliminate the commercial cost of these novel bioprosthesis making it more compatible with the existing bioprostheses. The large amount of incidentally killed animals during commercial fishing in the U.S.A. (approximately 40,000 per year), or i.e. the annual seal harvesting supported by Canadian Government for "population control" (approximately 150,000 per year) guarantee the stock of supply of this new bioprosthetic valve also.

As all marine mammals share essentially identical cardiac valve anatomy, the following species are included under the term "marine mammal" of the present invention: Harbor Seal (Phoca Vitulina); South American Fur Seal (Arctocephalus Australis); New Zealand Fur Seal, Western Australian Fur Seal (Arctocephalus Forsteri); Galapagos Fur Seal (Arctocephalus Galapogoensis); Kerguelen Fur Seal, Antarctic Fur Seal (Arctocephalus Gazella); Juan Fernandez Fur Seal (Arctocephalus Philippii); South African Fur Seal, Cape Fur Seal (Arctocephalus Pusillus); Amsterdam Island Fur Seal, Subantarctic Fur Seal (Arctocephalus Tropicalis); Northern Fur Seal (Callorhinus Ursinus); Hooded Seal, Bladdernose Seal (Cystophora Cristata); Bearded Seal (Erignathus Barbatus); California Sea Lion (Zalophus Californianus); Northern Sea Lion, Stella Sea Lion (Eunetopias Jubatus); Gray Seal (Halichoerus Grypus); Leopard Seal (Hydrurga Leptonyx); Atlantic White-sided Dolphin (Lagenorhynchus Acutus); Bottlenose Dolphin (Turiops Truncatus); Weddell Seal (Leptonychotes Weddelli); Crabeater Seal (Lobodon Carninophagus); Northern Right Whale Dolphin (Lissodelphis Borealis); Southern Right Whale Dolphin (Lissodelphis Peronii); Spectated Porpoise (Phocoena Dioptica); Harbor Porpooise (Phocoena Phocoena); Vaquita, Kochito (Phocoena Sinus); Northern Elephant Seal (Mirounga Angustirostris); Southern Elephant Seal (Mirounga Leonina); Mediterranean Monk Seal (Monachus Monachus); Hawaiian Monk Seal (Monachus Schauinslandi); Carribean Monk Seal, West Indian Monk Seal (Monachus Tropicalis); Australian Sea Lion (Neophoca Cinerea); Finless Porpoise (Neophocoena Phocoenoides); Ross Seal (Ommatophoca Rossii); South American Sea Lion (Otaria Flavescens); Caspian Seal (Phoca Caspica); Ribbon Seal (Phoca Fasciata); Harp Seal, Greenland Seal (Phoca Groelandica); Ringed Seal (Phoca Hispida); Largha Seal, Spotted Seal (Phoca Largha); Baikal Seal (Phoca Sibirica); Pacific Harbor Seal (Phoca Vitulina Richardi); Atlantic Hump-Backed Dolphin, West African Sousa (Souza Teuszii); Spotted Dolphin (Stenella Attenuata), Atlantic Spotted Dolphin (Stenella Longirostris); Beluga Whale (Delphinapterus Leucas)

It will be appreciated that modifications to the embodiments described in detail above, are of course possible. Accordingly, the present invention is not limited to the embodiments which have been described in detail above. For example, marine mammal tissues such as pericardium or fascia lata can be used to construct trileaflet bioprostheses, with techniques for example similar to those used for construction of bovine pericardial valves.

Accordingly, it can be seen that the present invention provides a method of treating human cardiac valve dysfunction, by replacing the existing valve with a novel bioprosthesis of the present invention which comprises a marine mammal ventricular outflow (aortic and pulmonary) valve. Preferably the marine mammal ventricular outflow valve has been treated with a fixative agent, such as glutaraldehyde, polyepoxy compounds or any other suitable agent, to fix the tissue valve, sterilize and at the same time to increase the valve strength and reduce the antigenicity of the tissue. The marine mammal ventricular outflow valve can be either stent-mounted by techniques analogous to that by which the already existing porcine aortic or bovine pericardial valves are stented, or it can be unstented.

The present invention therefore provides a bioprosthesis, comprising a marine mammal ventricular outflow (aortic and pulmonary) valve, which when unstented, is suitable for replacing the human aortic or pulmonary valves, or which, when stented, is suitable for replacing the human aortic, mitral or tricuspid valves. The method of replacing the human valves with the marine mammal ventricular outflow valve offers all the advantages of using bioprosthetic versus mechanical valves; in addition, eliminates a major disadvantage of the existing aortic porcine valves, which is the asymmetry of the cusps and the presence of the muscle shelf therein which results in restricted blood flow, and the disadvantage of the bovine pericardial valves that being artificial can not match the function and the properties of natural valves. Due to the thickness of the cusps or leaflets, the marine mammal ventricular outflow (aortic or pulmonary) valve will result in a valve of sufficiently increased durability for replacing the human valve, without the attendant disadvantages of a porcine aortic or bovine pericardial valve replacement.

Although the description above contains many specificities, these should not be construed as limiting the scope of the invention but as merely providing illustrations of some of the presently preferred embodiments of this invention. Various other embodiments and ramifications are possible within it's scope.

Thus the scope of the invention should be determined by the appended claims and their legal equivalents, rather than by the examples given.

I claim:

1. A method of treating a human patient, comprising:
   i. providing a marine mammal trileaflet valve, and
   ii. surgically implanting said valve in said patient.

2. The method of claim 1, wherein said patient's existing aortic valve is replaced with said marine mammal trileaflet valve.

3. The method of claim 1, wherein said patient's existing pulmonary valve is replaced with said marine mammal trileaflet valve.

4. The method of claim 1, wherein said marine mammal valve is a fixed and sterilized stent-mounted trileaflet valve.

5. The method of claim 1, wherein said marine mammal valve is a fixed and sterilized whole excised unstented trileaflet valve.

6. The method of claim 1 wherein said marine mammal trileaflet valve is a ventricular outflow valve.

7. The method of claim 1, wherein said marine mammal trileaflet valve is a bioprothesis constructed from marine mammal tissues selected from the group consisting of pericardium or fascia lata.

8. The method of claim 1, wherein said marine mammal valve comprises a section of ascending aorta.

9. The method of claim 1, wherein said marine mammal valve comprises a section of pulmonary artery.

10. The method of claim 1, wherein said marine mammal valve has an inlet side and further comprises a flexible sewing skirt extending from said inlet side to facilitate suturing of the valve in said patient.

11. A method of treating valve dysfunction in a human patient, comprising:
   i. providing a marine mammal ventricular outflow valve, and
   ii. replacing an existing dysfunctional aortic, mitral, tricuspid or pulmonary valve in said patient with said ventricular outflow valve.

12. The method of claim 11, wherein said marine mammal valve is a fixed and sterilized stent-mounted valve.

13. The method of claim 11, wherein said marine mammal valve is a fixed and sterilized unstented valve.

14. The method of claim 11, wherein said marine mammal valve comprises a bioprothesis constructed from marine mammal tissues selected from the group consisting of pericardium or fascia lata.

15. The method of claim 11, wherein said marine mammal valve comprises a section of ascending aorta.

16. The method of claim 11, wherein said marine mammal valve comprises a section of pulmonary artery.

17. The method of claim 11, wherein said marine mammal valve has an inlet side and further comprises a flexible sewing skirt extending from said inlet side to facilitate suturing of the valve in said patient.

18. A composition, consisting of a fixed, marine mammal ventricular outflow valve having a sewing skirt.

19. The composition of claim 18, wherein said valve is a sterilized whole excised unstented valve.

20. The composition of claim 18, wherein said marine mammal is selected from the group consisting of seals, sea lions, dolphins, porpoises, and whales.

21. An excised, marine mammal valve having an inlet side and further comprising a flexible sewing skirt extending from said inlet side, said flexible skirt configured so as to facilitate suturing of the valve in a patient.

22. The excised, marine mammal valve of claim 21, further comprising a section of ascending aorta.

23. The excised, marine mammal valve of claim 21, further comprising a section of pulmonary artery.

* * * * *

UNITED STATES PATENT AND TRADEMARK OFFICE
CERTIFICATE OF CORRECTION

PATENT NO.    : 6,165,216
DATED         : December 26, 2000
INVENTOR(S)   : Efstathios Andreas Agathos It is certified that error appears in the above-identified patent and that said Letters Patent is hereby corrected as shown below:

<u>Title page, Item [54] and Column 1, line 1,</u>
Title, after "HUMAN CARDIAC VALVE . . . ," please delete "PLACEMENT;" please insert -- REPLACEMENT --.

Signed and Sealed this

Third Day of February, 2004

JON W. DUDAS
*Acting Director of the United States Patent and Trademark Office*